(12) United States Patent
Balian

(10) Patent No.: US 7,323,542 B2
(45) Date of Patent: Jan. 29, 2008

(54) BONE TARGETING PEPTIDES

(75) Inventor: Gary Balian, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 25 days.

(21) Appl. No.: 10/503,574

(22) PCT Filed: Feb. 21, 2003

(86) PCT No.: PCT/US03/05470

§ 371 (c)(1),
(2), (4) Date: Aug. 4, 2004

(87) PCT Pub. No.: WO03/072593

PCT Pub. Date: Sep. 4, 2003

(65) Prior Publication Data

US 2005/0085623 A1  Apr. 21, 2005

Related U.S. Application Data

(60) Provisional application No. 60/359,008, filed on Feb. 21, 2002.

(51) Int. Cl.
*A61K 38/00* (2006.01)
(52) U.S. Cl. .......................................... 530/300; 514/2
(58) Field of Classification Search ..................... None
See application file for complete search history.

(56) References Cited

U.S. PATENT DOCUMENTS

| 5,683,459 | A | * | 11/1997 | Brekke | ...................... | 424/423 |
| 2003/0092077 | A1 | * | 5/2003 | Ramarao | ................... | 435/7.21 |
| 2003/0113714 | A1 | * | 6/2003 | Belcher et al. | ................ | 435/5 |

* cited by examiner

*Primary Examiner*—Cecilia Tsang
*Assistant Examiner*—Roy Teller
(74) *Attorney, Agent, or Firm*—Rodney L. Sparks

(57) ABSTRACT

The present invention relates to compositions comprising unique bone targeting peptides and the use of compositions comprising such peptides to induce bone repair and treat bone related diseases.

27 Claims, 1 Drawing Sheet

BONE TARGETING PEPTIDES

RELATED APPLICATIONS

This application claims priority under 35 U.S.C. §119(e) to provisional patent application No. 60/359,008, filed Feb. 21, 2002 the disclosure of which is incorporated herein by reference in its entirety.

FIELD OF THE INVENTION

The present invention is directed to bone trophic peptides identified through the use of a phage display library. More particularly, the invention is directed to compositions comprising the bone trophic peptides and methods for using such compositions to enhance bone repair and treat various bone related diseases.

BACKGROUND OF THE INVENTION

A limited number of proteins have been identified as being primarily associated with bone tissue. In addition, reports in the literature have presented compelling evidence that the targets of these proteins are receptors on the cell surface. Accordingly, applicants anticipate that protein domains may be responsible for targeting these proteins to cell receptors or receptor ligands in the extracellular matrix of the target tissue. Therefore these peptides could be used for a wide variety of therapeutic uses including the delivery of drugs that could help in the treatment of musculoskeltal disorders, genetic or acquired, osteoporosis and metastatic cancer. Furthermore it is anticipated that the peptides themselves can serve as therapeutic agents providing osteogenic or trophic activity for osteoblast, mesenchymal or hematopoietic cell lineages.

To detect peptides that are targeted to the bone, a phage display peptide library was prepared using a kit from New England Biolabs. The phage display library provides a selection technique wherein a peptide is expressed as a fusion protein with a bacteriophage coat protein, resulting in the display of the fused protein on the surface of the virion, while the DNA encoding that fusion protein resides within the virion. The phage peptide library is created using random nucleic acid sequences to generate fusion proteins that comprise the coat protein linked to a random peptide sequences. An in vitro or in vivo selection process designated "biopanning" is then conducted to identify those randomly generated peptides that bind to the target tissue. More particularly, the phage display library is contacted with the target cells, the unbound phage are washed away and the specifically bound phage are eluted. The eluted phage is then amplified and taken through addition binding/amplification cycles to enrich the pool in favor of binding sequences. Applicants have identified 14 peptides that are bone targeting peptides (see Example 1) and these peptides form the basis of the present invention.

SUMMARY OF THE INVENTION

The present invention is directed to a series of peptides that have been discovered to exhibit bone targeting properties. Compositions comprising these proteins have utility in promoting bone and cartilage repair through osteogenic and osteo-trophic effects. Furthermore these compounds can be coupled with other bioactive compounds as a means of delivering or retaining therapeutic agents at their target sites. In accordance with one embodiment the bone targeting peptides of the present invention are combined with a biodegradable carrier that is capable of releasing the peptides in a predictable and controlled rate.

DETAILED DESCRIPTION OF THE INVENTION

Definitions

Figure 1:
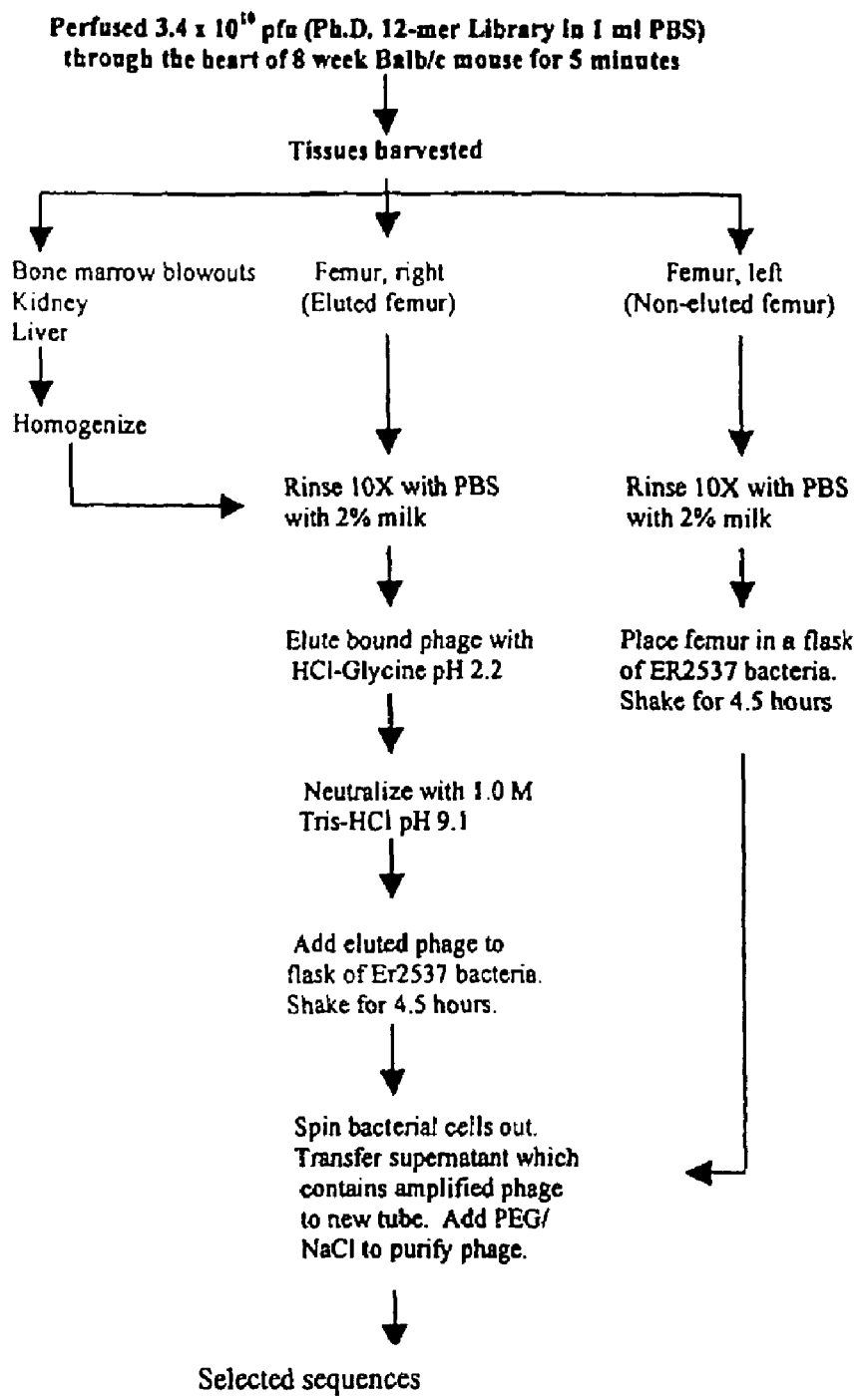
FIG. 1 shows a schematic of the experimental design for phage display.

In describing and claiming the invention, the following terminology will be used in accordance with the definitions set forth below.

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A."

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

The term "peptide" encompasses a sequence of 3 or more amino acids wherein the amino acids are naturally occurring or synthetic (non-naturally occurring) amino acids. Peptide mimetics include peptides having one or more of the following modifications:

1. peptides wherein one or more of the peptidyl —C(O)NR— linkages (bonds) have been replaced by a non-peptidyl linkage such as a —CH2-carbamate linkage (—CH$_2$OC(O)NR—), a phosphonate linkage, a —CH$_2$-sulfonamide (—CH$_2$—S(O)$_2$NR—) linkage, a urea (—NHC(O)NH—) linkage, a —CH$_2$-secondary amine linkage, or with an alkylated peptidyl linkage (—C(O)NR—) wherein R is $C_1$-$C_4$ alkyl;
2. peptides wherein the N-terminus is derivatized to a —NRR$_1$ group, to a —NRC(O)R group, to a —NRC(O)OR group, to a —NRS(O)$_2$R group, to a —NHC(O)NHR group where R and R$_1$ are hydrogen or $C_1$-$C_4$ alkyl with the proviso that R and R$_1$ are not both hydrogen;
3. peptides wherein the C terminus is derivatized to —C(O)R$_2$ where R$_2$ is selected from the group consisting of $C_1$-$C_4$ alkoxy, and —NR$_3$R$_4$ where R$_3$ and R$_4$ are independently selected from the group consisting of hydrogen and $C_1$-$C_4$ alkyl.

Naturally occurring amino acid residues in peptides are abbreviated as recommended by the IUPAC-IUB Biochemical Nomenclature Commission as follows: Phenylalanine is Phe or F; Leucine is Leu or L; Isoleucine is Ile or I;

Methionine is Met or M; Norleucine is Nle; Valine is Vat or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; Glycine is Gly or G, and X is any amino acid. Other naturally occurring amino acids include, by way of example, 4-hydroxyproline, 5-hydroxylysine, and the like.

As used herein, the term "conservative amino acid substitution" is defined herein as exchanges within one of the following five groups:

I. Small aliphatic, nonpolar or slightly polar residues:

Ala, Ser, Thr, Pro, Gly;

II. Polar, negatively charged residues and their amides:

Asp, Asn, Glu, Gln;

III. Polar, positively charged residues:

His, Arg, Lys;

IV. Large, aliphatic, nonpolar residues:

Met Leu, Ile, Val, Cys

V. Large, aromatic residues:

Phe, Tyr, Trp

As used herein the term "solid support" relates to a solvent insoluble substrate that is capable of forming linkages (preferably covalent bonds) with soluble molecules. The support can be either biological in nature, such as, without limitation, a cell or bacteriophage particle, or synthetic, such as, without limitation, an acrylamide derivative, glass, plastic, agarose, cellulose, nylon, silica, or magnetized particles. The support can be in particulate form or a monolythic strip or sheet. The surface of such supports may be solid or porous and of any convenient shape.

As used herein, the term "purified" and like terms relate to the isolation of a molecule or compound in a form that is substantially free (at least 60% free, preferably 75% free, and most preferably 90% free) from other components normally associated with the molecule or compound in a native environment.

The term "disease state" is intended to encompass any condition that is associated with an impairment of the normal state of a living animal or plant including congenital defects, pathological conditions such as cancer, and responses to environmental factors and infectious agents (bacterial, viral, etc.).

"Therapeutic agent," "pharmaceutical agent" or "drug" refers to any therapeutic or prophylactic agent which may be used in the treatment (including the prevention, diagnosis, alleviation, or cure) of a malady, affliction, disease or injury in a patient.

As used herein, the term "treating" includes alleviating the symptoms associated with a specific disorder or condition and/or preventing or eliminating said symptoms. For example, treating cancer includes preventing or slowing the growth and/or division of cancer cells as well as killing cancer cells.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, the term "antibody" refers to a polyclonal or monoclonal antibody or a binding fragment thereof such as Fab, F(ab')$_2$ and Fv fragments.

As used herein, the term "parenteral" includes administration subcutaneously, intravenously or intramuscularly.

The term "biocompatible", as used herein, refers to a material that does not elicit a substantial detrimental response in the host.

As used herein the term "bioactive agent" refers to substances which are capable of exerting a biological effect in vitro and/or in vivo.

The Invention

The present invention is directed to the identification of peptides that target bone, biocompatible compositions comprising those peptides and methods for using such compositions for treating damaged or diseased bone or cartilage tissues. The bone targeting peptides were identified using a phage display library (using the general procedure described in Example 1) based on their ability to bind and become localized to bone tissue after general injection into a mouse. Accordingly one aspect of the present invention is directed to purified peptides comprising the following sequences:

```
                                            (SEQ ID NO:1)
THR-MET-ARG-ASN-PRO-ILE-THR-SER-LEU-ILE-SER-VAL-
GLY-GLY-GLY-SER (SEQ ID NO:2)
LEU-LEU-ALA-ASP-THR- THR-HIS-HIS-ARG-PRO-TRP-THR-
GLY-GLY-GLY-SER (SEQ ID NO:3)
LYS-GLU-ILE-PRO-PRO-ILE-PRO-LEU-LEU-ALA-PRO-SER-
GLY-GLY-GLY-SER, (SEQ ID NO:4)
ASN-ASN-VAL-SER-GLN-LYS-TRP-GLN-GLN-ARG-LEU-ILE-
GLY-GLY-GLY-SER, (SEQ ID NO:5)
ASN-SER-MET-ILE-ALA-HIS-ASN-LYS-THR-ARG-MET-HIS-
GLY-GLY-GLY-SER, (SEQ ID NO:6)
GLY-ILE-HIS-VAL-PRO-TRP-MET-PRO-PRO-VAL-ALA-PHE-
GLY-GLY-GLY-SER, (SEQ ID NO:7)
GLN-ARG-SER-TRP-THR-LEU-ASP-SER-ALA-LEU-SER-MET-
GLY-GLY-GLY-SER, (SEQ ID NO:8)
SER-GLY-HIS-GLN-LEU-LEU-LEU-ASN-LYS-MET-PRO-ASN-
GLY-GLY-GLY-SER, (SEQ ID NO:9)
SER-SER-THR-LEU-LYS-THR-PHE-PHE-GLY-PHE-PRO-ASP-
GLY-GLY-GLY-SER, (SEQ ID NO:10)
ASP-SER-SER-ASN-PRO-ILE-PHE- TRP-ARG-PRO-SER-SER-
GLY-GLY-GLY-SER,
```

-continued (SEQ ID NO:11)
ASN-TYR-SER-HIS-LEU-ARG- VAL-LYS-LEU-PRO-THR-PRO-GLY-GLY-GLY-SER, (SEQ ID NO:12)
SER-GLY-HIS-GLN-LEU-LEU-LEU-ASN-LYS-MET-PRO-ASN-GLY-GLY-GLY-SER, (SEQ ID NO:13)
ALA- THR-TRP-SER-HIS-HIS-LEU-SER-SER-ALA-GLY -LEU-GLY-GLY-GLY-SER, (SEQ ID NO:14)
SER-TYR-SER-GLN-MET-ASP-PRO-PRO-ARG-SER-LEU-PRO-GLY-GLY-GLY-SER, (SEQ ID NO:15)
THR-MET-ARG-ASN-PRO-ILE-THR-SER-LEU-ILE-SER-VAL, (SEQ ID NO:16)
LEU-LEU-ALA-ASP-THR- THR-HIS-ARG-PRO-TRP-THR, (SEQ ID NO:17)
LYS-GLU-ILE-PRO-PRO-ILE-PRO-LEU-LEU-ALA-PRO-SER, (SEQ ID NO:18)
ASN-ASN-VAL-SER-GLN-LYS-TRP-GLN-GLN-ARG-LEU-ILE, (SEQ ID NO: 19)
ASN-SER-MET-ILE-ALA-HIS-ASN-LYS-THR-ARG-MET-HIS, (SEQ ID NO:20)
GLY-ILE-HIS-VAL-PRO-TRP-MET-PRO-PRO-VAL-ALA-PHE, (SEQ ID NO:21)
GLN-ARG-SER-TRP-THR-LEU-ASP-SER-ALA-LEU-SER-MET, (SEQ ID NO:22)
SER-GLY-HIS-GLN-LEU-LEU-LEU-ASN-LYS-MET-PRO-ASN, (SEQ ID NO:23)
SER-SER-THR-LEU-LYS-THR-PHE-PHE-GLY-PHE-PRO-ASP, (SEQ ID NO:24)
ASP-SER-SER-ASN-PRO-ILE-PHE- TRP-ARG-PRO-SER-SER, (SEQ ID NO:25)
ASN- TYR-SER-HIS-LEU-ARG- VAL-LYS-LEU-PRO-THR-PRO, (SEQ ID NO:26)
SER-GLY-HIS-GLN-LEU-LEU-LEU-ASN-LYS-MET-PRO-ASN, (SEQ ID NO:27)
ALA- THR- TRP-SER-HIS-HIS-LEU-SER-SER-ALA-GLY-LEU, and (SEQ ID NO:28)
SER-TYR-SER-GLN-MET-ASP-PRO-PRO-ARG-SER-LEU-PRO as well as bioactive fragments and derivatives of SEQ ID NOs: 15-28 that exhibit bone targeting properties. Derivatives of SEQ ID NOs: 15-28 include amino acid sequences that differ from those sequences either by one or more conservative amino acid substitutions, or by one amino acid deletion, addition or substitution. In one embodiment the peptides comprise a sequence identical to SEQ ID NO: 15-24, or differ from SEQ ID NO: 15-24 by 1-2 conservative amino acids.

In accordance with one embodiment a peptide is provided having a maximum length of 25 amino acids and comprising an amino acid sequence selected from the group consisting of SEQ ID NO: 15-24. In one embodiment the bone targeting protein consists of an amino acid sequence selected from the group consisting of SEQ ID NO: 15-24. The peptides can be prepared from natural proteins, produced recombinantly or more preferably they are chemically synthesized using techniques well know to those skilled in the art. In one embodiment the purified peptide comprises an amino acid sequence selected from the group consisting of SEQ ID NO: 22, SEQ ID NO: 24, SEQ ID NO: 25 and SEQ ID NO: 27, and in one example the peptide comprises amino sequence of SEQ ID NO: 22. The present invention is also directed to antibodies that specifically bind to a peptide selected from the group consisting of SEQ ID NOs: 15-24.

The present invention also encompasses pharmaceutical and therapeutic compositions comprising the bone targeting peptides of the present invention. In accordance with one embodiment the present invention is directed to a composition comprising a purified peptide comprising a sequence identical to SEQ ID NO: 15-24, or differing from SEQ ED NO: 15-24 by 1-2 conservative amino acids, and a biocompatible material. In one embodiment the biocompatible material constitutes a pharmaceutically acceptable carrier. Alternatively, the biocompatible material may comprise a solid carrier or polymer matrix, wherein the bone targeting peptide is entrapped within the carrier or matrix or otherwise bound to the surface of the carrier or matrix. In one embodiment the composition comprises a bone targeting peptide of the present invention and a bioresorbable/biodegradeable polymer matrix, wherein the polymer matrix provides timed release of the bioactive peptides.

Many matrix systems have been developed to contain and then steadily release bioactive peptides as the matrix degrades. Organic polymers such as polylactides, polyglycolides, polyanhydrides, and polyorthoesters, which readily hydrolyze in the body into inert monomers, have been used as matrixes (see U.S. Pat. Nos. 4,563,489; 5,629,009; and 4,526,909). The efficiency of peptide release from polymer matrixes depends on the matrixes resorbtion rate, density, and pore size. Monomer type and their relative ratios in the matrix influence these characteristics. Polylactic and polyglycolic acid copolymers, protein sequestering agents, and osteoinductive factors provide the necessary qualities for a bioactive peptide delivery system (see U.S. Pat. No. 5,597, 897). Alginate, poly(ethylene glycol), methyl methacrylate, polyoxyethylene oxide, carboxyvinyl polymer, and poly (vinyl alcohol) are additional polymer examples that can be used in accordance with the present invention.

Non-synthetic matrix proteins like collagen, glycosaminoglycans, and hyaluronic acid, which are enzymatically digested in the body, have also been used to deliver bioactive proteins to bone areas (see U.S. Pat. Nos. 4,394,320; 4,472, 840; 5,366,509; 5,606,019; 5,645,591; and 5,683,459) and are suitable for use with the present invention. The bone targeting peptide compositions can be further combined with a demineralized bone material, growth factor, nutrient factor, pharmaceutical, calcium-containing compound, anti-inflammatory agent, antimicrobial agent, or any other substance capable of expediting or facilitating bone growth. Examples of osteoinductive factor suitable for use with the compositions of the present invention include demineralized bone particles, a Bone Morphogenetic Protein, an osteoinductive extract of demineralized bone matrix, or a combination thereof.

Examples of growth factors suitable for use with the composition of the present invention include Transforming Growth Factor-Beta (TGF-.beta.), Transforming Growth Factor-Alpha (TGF-.alpha.), Epidermal Growth Factor (EGF), Insulin Like Growth Factor-I or II, Interleukin-I (IL-I), Interferon, Tumor Necrosis Factor, Fibroblast Growth Factor (FGF), Platelet Derived Growth Factor (PDGF), and Nerve Growth Factor (NGF).

The compositions of the present invention can also be combined with inorganic fillers or particles. For example for use in implantable grafts the inorganic fillers or particles can be selected from hydroxyapatite, tri-calcium phosphate, ceramic glass, amorphous calcium phosphate, porous ceramic particles or powders, mesh titanium or titanium alloy, or particulate titanium or titanium alloy.

In accordance with one embodiment of the invention a method is provided for treating cancer, particularly bone cancers and cancers that metastasize to the bone (e.g. prostate cancer). The method comprises the steps of administering a peptide selected from the group consisting of SEQ ID NOs: 15-28 to a patient in need thereof. In one embodiment a composition comprising these peptides is administered locally by injection. Compositions comprising the peptides of SEQ ID NOs: 15-28 can be further combined with other known anti-cancer agents, including cytotoxic agents, and in one embodiment the anti-cancer agents are covalently bound to the peptides. These compositions can be prepared in the form of an implantable device that can be molded to a desired shape. In one embodiment a graft construct is prepared comprising a biocompatible matrix and one or more of the bone targeting peptides of the present invention, wherein the matrix is formed in a shape to fill a gap or space created by the removal of a tumor or diseased tissue. Preferably the matrix material will provide a time release of the bioactive proteins as a further countermeasure to prevent reestablishment of the excised tumor or diseased tissue.

In accordance with one embodiment the bone targeting peptides of the present invention are complexed or linked to one or more bioactive agents. The bioactive agents can be linked to the bone targeting peptides through hydrogen, ionic, or covalent bonding. In one preferred embodiment the bioactive agent is covalently linked to the bone targeting peptides of the present invention. Also in accordance with this invention is the use of indirect means for associating the bioactive agents with the peptides including by connection through intermediary linkers, spacer arms, bridging molecules, or liposome entrapment. In one embodiment the peptide/bioactive agent complex can be used to deliver therapeutic pharmaceuticals to bone or cartilage tissues, wherein the bioactive agents are encapsulated within the liposome. Bioactive agents suitable for use with the present invention include antibodies, growth factors, toxins (such as aflatoxin, digoxin, xanthotoxin, rubratoxin), antibacterial agents (such as cephalosporins, penicillin, erythromycin, ciprofloxacin, cinoxacin, and norfloxacin), cancer drugs (including chemotherapeutic agents) and nucleic acids. In one embodiment the bone targeting protein is linked to a chemotherapeutic agent or other cancer drug and the complex is used to treat a patient suffering from cancer, especially bone cancer or cancer that has metastasized to bone or cartilagenous tissues.

In another embodiment of the present invention a method is provided for identifying and isolating the putative receptors for the bone targeting peptide sequences. The method comprises identifying the putative receptors by affinity chromatography and by two-dimensional peptide mapping of cell membrane proteins and extracellular matrix molecules. More particularly, the peptides of SEQ ID NOs: 1-24 will be immobilized on a solid support and the peptides will then be contacted with cell membrane proteins and extracellular matrix molecules to identify molecules that specifically bind to the bone targeting peptides.

The bone targeting peptides can be used in a variety of therapeutic applications. For example, for those individual peptides that are found to bind specifically to cells or extracellular matrix in bone, their potential as carriers of pharmacologic agents, such as polypeptide factors and therapeutic genes, can be explored. Determination of the effects of trophic peptides on cell attachment and invasion is particularly relevant to the cancer field. Identification of targeting peptides and their ligands will provide basic information towards understanding the mechanisms of metastases to bone.

Factors that target bone may have several beneficial effects. Implications to cancer metastases to bone is a prominent consideration since prostate cancer cells primarily target bone, as do breast cancer cells. Contributions to our understanding of cancer cell homing to bone may be forthcoming from the identification of the targets in bone that serve as the destination for the peptides. If the targets are ligands to the bone targeting peptide and appear on the surface of cells or in the extracellular matrix to bone, their identification will serve as a crucial step towards understanding important events in the overall mechanism of cancer cell metastasis. The peptides identified in the present application may mimic the segment of a protein on the cancer cell surface that exhibits bone targeting characteristics. This information could be an essential part of the effort contributing towards understanding mechanisms that underlie cell adhesion and invasion in cancer. In addition, identification of the target ligand in bone cells or in bone matrix, may yield valuable information as to why prostate and breast cancer cells target bone preferentially over other tissues.

In accordance with one embodiment a method for inhibiting the growth of tumors is provided. The method comprises the steps of contacting tumor cells with a composition comprising an amino acid sequence selected from the group consisting of SEQ ID NOs: 1-24. As described in Example 3 the peptides of the present invention have been studied for their ability to prevent cancer cells from binding to human bone marrow endothelial cells (huBMEC). Either androgen dependent cancer cells (LNCaP cells) or androgen independent cancer cells (C42 cells) were labeled with 3H-thymidine and placed in contact with huBMEC in the presence of varying concentrations of bone targeting peptides R1 (SEQ ID NO: 25), R3 (SEQ ID NO: 27), L13 (SEQ ID NO: 22) and L19 (SEQ ID NO: 24). The cells were washed and the percent of acid precipitatable counts bound to huBMEC was determined (See Table 1). The control, where no bone targeting peptide was added generated approximately 18% acid ppt counts bound. Based on this data, it appears that both peptides R3 and L13 substantially inhibits the ability of LNCaP and C42 cells to bind to huMEEC. Furthermore peptide L19 substantially inhibits the ability of C42 cells (but not LNCaP cells) to bind to huMEEC. Accordingly, these peptides in particular may be formulated a pharmaceutical compositions to prevent metastases to the bone. The composition may further include known anti-cancer agents such as chemotherapeutic agents. The compositions can be administered to a patient using any of the standard routes including oral and parenteral. In one preferred embodiment the compositions are administered locally by injection.

TABLE 1

PERCENT OF CONTROL AT 2H ADHESION

| | R1 50 µM | R1 100 µM | R3 50 µM | R3 100 µM | L13 50 µM | L13 100 µM | L19 50 µM | L19 100 µM |
|---|---|---|---|---|---|---|---|---|
| LNCaP | | | | | | | | |
| % of control | 14.7 | 9.9 | 14.7 | 3.8 | 3.8 | 2.8 | 3.3 | 4.1 |
| C4-2 | | | | | | | | |
| % of control | 9.0 | 9.6 | 17.9 | 7.9 | 5.8 | 4.2 | 15.6 | 18.4 |

In one embodiment the bone targeting proteins of the present invention are utilized to enhance bone and cartilage repair and regeneration. The peptides of the present invention are trophic to bone and thus are anticipated to have significant utility in the practice of Orthopaedic Surgery, particularly in the use of prostheses that can be indwelling for years if not decades. The biomimetic properties of bone trophic factors could create a technological step forward in the field of tissue engineering, as well as for prosthetic surgery of bone. Inclusion of bone targeting factors in synthetic or natural polymers may assist specificity of cell adherence, thereby scavenging endogenous cells within tissues that are undergoing repair and regeneration. The imbalance between bone formation and resorption, will be an equally important consideration for potential uses of the present trophic factors in musculoskeletal surgery, in addition to the relevance of this topic to cancer cell metastases.

There are several other implications to the discovery of peptides that target bone, particularly if the peptides are merely targeting bone matrix or cells without having a direct effect on metabolic properties at their destinations. For example, peptides could be used to target areas of bone lysis or of bone loss, thereby serving as carriers towards selected addresses in the skeleton. These characteristics can then be exploited by coupling drugs, such as growth factors, or genes to the trophic peptides, as a means of targeting pharmaceuticals to specific destinations in the skeleton, thereby raising a number of possibilities for therapeutic intervention for cancer metastases as well as for skeletal repair and regeneration.

One aspect of the present invention relates to osteogenic devices, and more specifically to synthetic implants which induce osteogenesis in vivo in mammals, including humans. More particularly, this embodiment of the invention relates to biocompatible, bioresorbable, synthetic compositions comprising the bone targeting proteins disclosed herein. These compositions are anticipated to have osteogenic properties and/or are trophic for osteogenic cell images. The implants can be prepared using previously described implant materials such as hydroxlapatite, autogenous bone grafts, allogenic bone matrix, demineralized bone powder, collagenous matrix. The bone targeting peptides of the present invention can be combined with know graft materials that are fully formable at a temperatures above 38° C. but becoming a solid at temperatures below when it falls below 38° C. Such compositions such as Opteform 100HT (University of Florida Tissue Bank) comprise a thermoplastic human derived inert carrier allowing the material stays rigid once it reaches body temperature. In another embodiment the bone targeting peptides are combined with known materials to provide a composition for coating implantable prosthetic devices, and to increase the cellular ingrowth into such devices.

In one aspect of the invention the matrix material is provided as a coating on an implant placed in contact with viable bone. Useful implants are composed of an inert material such as ceramic, glass, metal, or polymer. In another aspect of the invention, bone growth is induced from a viable mammalian bone by contacting the bone with matrix material comprising a bone targeting peptide, into which has been dispersed a glue in an amount sufficient to solidify the matrix when implanted in a mammal or when placed at 37° C. One glue suitable for such use is methyl cellulose. The matrix solidifies substantially in the shape of the implanted matrix.

EXAMPLE 1

Isolation of Bone Targeting Peptides through the use of Phage Display Libraries

To isolate bone targeting peptides a phage display library was prepared containing randomly generated sequences (New England Biolabs). The phage display library provides a selection technique wherein a peptide is expressed as a fusion protein with a bacteriophage coat protein, resulting in the display of the fused protein on the surface of the virion, while the DNA encoding that fusion protein resides within the virion. More particularly, phage display library kit is based on a combinatorial library of random peptide 12-mers fused to a minor coat (pIII) of M13 phage. The displayed peptide 12-mers are expressed at the N-terminus of pill, i.e., the first residue of the mature protein is the first randomized position. The peptide is followed by a short spacer (Gly-Gly-Gly-Ser) and then the wild-type III sequence. The library consists of ~2.7×10$^9$ electroporated sequences, amplified once to yield ~55 copies of each sequence.

An in vitro or in vivo selection process, designated "biopanning," is then conducted to identify those randomly generated peptides that bind to the target tissue. A schematic representation of that process is provided in FIG. 1. More particularly, the phage display library is injected into mice, the mice are euthanized and the femors recovered. The recovered femors are then washed to remove unbound phage and then the specifically bound phage is recovered. The eluted phage is the amplified and taken through addition binding/amplification cycles to enrich the pool in favor of binding sequences. After 3-4 rounds, individual clones are characterized by DNA sequencing and is injected into a mouse. Bone tissue is then isolated from the mouse and the associated phage recovered and the proteins identified through DNA sequencing this procedure has identified the peptides of SEQ ID NOs: 1-14 as bone targeting peptides. The sequences were detected repeatedly in phage that was isolated from bone and bone marrow.

One objective of the present invention is directed to the identification of peptides sequences that target cells within bone and bone marrow, such as osteoblasts, osteoblast progenitors (i.e. mesenchymal cells in bone marrow stroma), hematopoietic cells or endothelial cells in the endosteal lining, and, to determine the effect of peptides on prostate cancer cell adhesion and invasion. To determine tissue targeting specificity, binding of the phage peptide library to spleen, liver, lung and to musculoskeletal tissues other than bone, will be examined.

EXAMPLE 2

Binding of Peptides to Cells In Vitro

The cells currently investigated for binding to the peptides of the present invention were chosen because they are derived from bone marrow and are characteristic of mesenchymal cells that are pluripotential and behave as osteoprogenitors. The cells are capable of differentiating into bone cells in vitro and retain their osteogenic properties after transplantation in vivo into syngeneic mice. The human bone marrow endothelial cells are non-osteogenic and, therefore, are in contrast to the collagen type I, and mineral, producing properties of mesenchymal cells. The bone marrow endothelial cells serve the purpose of having a cell that is derived from the endothelial lining of the bone marrow cavity i.e. a cell from the endosteal surface. Although these are not the only cells that can be used, they will form the basis of the majority of the present studies with cells. Cells from bone matrix (osteoblasts) will be prepared and tested for comparison with the mesenchymal and the endothelial cells to determine similarities and differences between them and the cell lines that are available.

Peptides have been synthesized with a gly-gly-gly linker and coupled to biotin. Detection with avidin-FITC and visualization using an epifluorescence microscope has become routine in our laboratory. The cells are incubated with peptide at 4 degrees centigrade to minimize internalization of peptide. Following this incubation the cells are fixed with paraformaldehyde or further incubated without fixation with aldehyde. Avidin-FITC has been found on cells in two out of the three peptides that were tested so far. Fluorescence was found at attachment sites of cellular processes to the substratum. This may indicate that the peptide target adhesion plaques or cell footprints.

To assure specificity of cell and tissue binding, cell adhesion and invasion and the identification of cell surface and extracellular matrix ligands, the peptide sequences will be scrambled to generate random sequences that are unrecognizable compared with the original sequence of each peptide, except for their amino acid compositions. The corresponding peptide with scrambled sequence will help to assure specificity of binding by the peptide under study to their targets.

Control experiments with non-biotinylated peptides will ensure that binding avidin-FITC is specific to the properties of the peptide that target the cell surface or its extracellular matrix. No non-specific binding has been encountered so far with the three peptide sequences that have been explored and, there was no background fluorescence.

The peptides may have different effects depending on cell types from different tissues. The need to explore cells from other tissues, such as fibroblasts, adipocytes or muscle cells, may be determined by the location of the peptide ligands in area of tissue that are not directed within bone but there are adjacent to it. The case in point is that one peptide so far, L19, has been located to a tissue, that has not been identified yet, which, is adjacent to bone in rib. By contrast, L13 binds to rib bone and, and R1 binds to cells in culture. Analysis of cell types other than marrow mesenchymal or endothelial cells will help identify the specific cells, and their matrices that are targeted by individual peptides. Peptide L19 has been localized to a soft tissue adjacent to rib Peptide L13 binds to bone (in rib), and peptide L19 has been preliminarily localized to a soft tissue, that is associated with rib, but is not detected in the bone itself.

EXAMPLE 3

Bone Targeting Peptide Interference with Cancer Cell Binding to Bone Cells

Prostate cancer metastases are found in the bone at high frequency. To study further the interaction of prostate cancer cells with the bone and metastasis to bone, the LNCaP human prostate cancer progression model was developed. An additional cancer cell line, C4-2B is known to metastasize spontaneously to the marrow regions of the lumbar spine in athymic male mouse hosts that results in cord compression and paraplegia. This property was utilized to develop a direct intraosseous xenograft model to allow for more rapid assessment of prostate: bone interaction and evaluation of therapeutic intervention in preclinical trials. More recently, we have begun to examine the mechanism for prostate cancer's predilection for bone metastasis using in vitro models of adhesion and invasion. The targets for prostate cell adhesion are both putative sites of CaP cell interaction with bone, 1) fetal mouse preosteoblasts, D1 and 2) human bone marrow endothelial cells, huBMEC. The results of these studies have shown reproducible, significant differences in the adhesion and invasion of prostate cancer cells to D1 and huBMEC cells.

Adhesion Assays.

The initial interaction of metastatic cells is with the surface of the organ that will be colonized. Presumably, this interaction is through cell-matrix or cell-cell interaction. There are at least two potential targets for prostate cancer cells to interact, bone stromal cells and bone marrow endothelial cells. Briefly, lawns of target cells (D1 or huBMEC) will be established in 24-well dishes by seeding ~$5\times10^4$ cells per well 2-3 days before the adhesion experiment. At this time, subconfluent (~50%) cultures of test cells (LNCaP, C4-2, DU145 and PC-3) will be placed into media with 1 uCi/ml tritiated thymidine. Two to three days later, labeled cells will be removed using a 5-10 mM EDTA/PBS solution and $1\times10^5$ test cells will be added to confluent lawns of target cells. Three groups are envisioned for each cell line 1) no peptide, 2) peptide at ED50 and 3) peptide at ED90.

There will also be an aliquot of labeled cells set aside to determine total acid precipitable counts added. Adhesion assays will proceed for either 1 or 2 hours. Adherent cells will be separated from non-adherent cells by 2 rounds of 0.5 ml washes with PBS at 100 rpm for 2 minutes per wash. The remaining cells will then be fixed in 10% TCA for 10 min. with gentle shaking followed by hydrolysis of the residue in 0.5 ml of 2 N NaOH. The NaOH will be neutralized by 100 ul of concentrated HCl. The samples will then be counted in a liquid scintillation apparatus. The data will be analyzed by the Mellon Prostate Center Biostatistics Core to determine differences in growth and the ED50 and ED90 for each peptide if reasonable.

Using this adhesion assay the bone targeting peptides have been studied for their ability to prevent cancer cells from binding to huBMEC. Either androgen dependent cancer cells (LNCaP cells) or androgen independent cancer cells (C42 cells) were labeled with 3H-thymidine and placed in contact with huBMEC in the presence of varying concentrations of bone targeting peptides R1 (SEQ ID NO: 25), R3 (SEQ ID NO: 27), L13 (SEQ ID NO: 22) and L19 (SEQ ID NO: 24). The cells were washed and the percent of acid precipitatable counts bound to huBMEC was determined (See Table 1). The control, where no bone targeting peptide was added, is not shown, but generated approximately 18% acid ppt counts bound. Based on this data, it appears that both peptides R3 and L13 substantially inhibits the ability of LNCaP and C42 cells to bind to huMEEC. Furthermore peptide L19 substantially inhibits the ability of C42 cells (but not LNCaP cells) to bind to huMEEC. Accordingly, these peptides in particular may be formulated a pharmaceutical compositions to prevent metastases to the bone.

In order to determine whether the phage-derived peptides have a direct effect on prostate cell growth and viability, we will perform growth assays and cell death assays in response to phage-derived peptide treatment in vitro. Prostate cells will be grown in 24-well dishes in the presence of escalating dosages of each peptide in triplicate (0, 0.1 nM, 0.5 nM, 1 uM, 5 uM, 10 uM, 50 uM and 100 uM) to determine the effect of peptide on CaP cell growth and viability. The CaP cells will be plated at 10,000 cells (LNCaP, C4-2) or 5,000 cells/well (PC-3, DU145) and allowed to recover overnight. The following day the media will be changed and each well will be given either a control solution or a dose of phage-derived peptide. The cells will be treated in triplicate with one control and seven dosages of peptide per plate. The media and treatments will be changed every other day.

Assay endpoints are day 1, 3, 5 and 7 of treatment. Relative growth will be determined using crystal violet assay. The data will be analyzed by the Mellon Prostate Center Biostatistics Core to determine differences in growth and the ED50 and ED90 for each peptide if reasonable. Should the peptides prove to be effective at reducing cell growth, then subsequent experiments will be performed to determine if this happens via apoptotic death pathway.

Nucleosome release assays (Roche BMB) will be performed according to the manufacturer's recommendations using untreated versus peptide treated cultures (at the ED50 and ED90) to distinguish whether the diminished cell numbers are cytostatic or due to an elevated rate of apoptosis. Subaim b. Adhesion and invasion assays will be performed on each peptide at the ED50 and ED90, as determined in subaim a1.

Invasion Assays.

Following the initial adhesion of a cancer cell to a target, the cancer cell must invade the tissue and establish a colony. Prostate cancer cells have been shown to express a variety of matrix degrading enzymes including urokinase, matrilysin, and type IV collagenase. The expression of some of these enzymes has been correlated to the invasive potential of CaP cells. The adhesion assays are designed to test the ability of phage-derived peptides to prevent or slow the invasion of prostate cancer cells through a bone marrow endothelial cell layer. Cells will be prepared as for adhesion layers, except that the lawns will be established using 50,000 huBMEC on 8 um pore transwell inserts for only 24-36 hours before use. Invasion assays will be 8 or 16 hours in duration. The migration of counts through the membrane will be monitored. The data will be expressed percent counts migrated per unit time according to the formula (counts migrated/counts migrated+counts in top*100). The data will be analyzed by the Mellon Prostate Center Biostatistics Core to determine differences in growth and the ED50 and ED90 for each peptide if reasonable.

The invention claimed is:

1. A purified peptide comprising an amino acid sequence selected from the group consisting of SEQ ID NO: 15, SEQ ID NO: 17, SEQ ID NO: 18, SEQ ID NO: 19, SEQ ID NO: 20, SEQ ID NO: 21, SEQ ID NO: 23, SEQ ID NO: 25, SEQ ID NO: 26, and SEQ ID NO: 28.

2. The peptide of claim 1 wherein the amino sequence is selected from the group consisting of SEQ ID NO: 22, SEQ ID NO: 24, SEQ ID NO: 25 and SEQ ID NO: 27.

3. The peptide of claim 1 wherein the amino acid is SEQ ID) NO: 22 or SEQ ID NO: 27.

4. A purified peptide consisting of an amino acid sequence selected from the group consisting of SEQ ID NO:15, SEQ ID NO: 17, SEQ ID NO: 18, SEQ ID NO: 19, SEQ ID NO: 20, SEQ ID NO: 21, SEQ ID NO: 23, SEQ ID NO: 25, SEQ ID NO: 26, SEQ ID NO: 28, further comprising a bioactive compound linked to said peptide further comprising a bioactive compound linked to said peptide.

5. The peptide of claim 4 wherein the bioactive compound is covalently bound to said peptide.

6. The peptide of claim 5 wherein the bioactive agent is selected from the group consisting of chemotherapeutics, nucleic acid sequences.

7. A composition comprising the peptide of claim 1 and a biocompatible material.

8. The composition of claim 7 wherein the biocompatible material comprises a pharmaceutically acceptable carrier.

9. The composition of claim 7 wherein the biocompatible material is a polymer matrix and said peptide and the matrix is coated onto an implantable prosthesis.

10. The composition of claim 7 wherein the biocompatible material comprises a delivery vehicle.

11. The composition of claim 10 wherein the delivery vehicle is a biodegradable polymer.

12. A method for enhancing bone repair, said method comprising the step of contacting a site in need of repair tissue with a composition comprising the peptide of claim 1.

13. The method of claim 12 wherein the composition is in an injectable form and the step of contacting the site comprises administering the composition locally by injection.

14. The method of claim 12 wherein the step of contacting the site comprises surgically implanting the composition.

15. The peptide of claim 1 wherein the amino acid sequence is SEQ ID NO: 19 or SEQ ID NO: 25.

16. The peptide of claim 15 wherein the amino acid sequence is SEQ ID NO: 19.

17. A composition comprising the peptide of claim 1 and a biocompatible material.

18. The composition of claim 17 wherein the biocompatible material comprises a pharmaceutically acceptable carrier.

19. The composition of claim 17 wherein the biocompatible material is a polymer matrix and said peptide in and the matrix is coated onto an implantable prosthesis.

20. The composition of claim 17 wherein the biocompatible material comprises a delivery vehicle.

21. The composition of claim 20 wherein the delivery vehicle is a biodegradable polymer.

22. The composition of claim 17, wherein the amino acid sequence is SEQ ID NO: 19 or SEQ ID NO: 25.

23. The composition of claim 22, wherein the amino acid sequence is SEQ ID NO: 19.

24. The composition of claim 23 wherein the biocompatible material comprises a pharmaceutically acceptable carrier.

25. The composition of claim 23 wherein the biocompatible material is a polymer matrix and said protein and the matrix is coated onto an implantable prosthesis.

26. The composition of claim 23 wherein the biocompatible material comprises a delivery vehicle.

27. The composition of claim 26 wherein the delivery vehicle is a biodegradable polymer.

* * * * *

SEQUENCE LISTING

```
<160> NUMBER OF SEQ ID NOS: 28

<210> SEQ ID NO 1
<211> LENGTH: 12
<212> TYPE: PRT
<213> ORGANISM: Homo sapiens

<400> SEQUENCE: 1

Thr Met Arg Asn Pro Ile Thr Ser Leu Ile Ser Val
1               5                   10

<210> SEQ ID NO 2
<211> LENGTH: 16
<212> TYPE: PRT
<213> ORGANISM: Homo sapiens

<400> SEQUENCE: 2

Leu Leu Ala Asp Thr Thr His His Arg Pro Trp Thr Gly Gly Gly Ser
1               5                   10                  15

<210> SEQ ID NO 3
<211> LENGTH: 16
<212> TYPE: PRT
<213> ORGANISM: Homo sapiens

<400> SEQUENCE: 3

Lys Glu Ile Pro Pro Ile Pro Leu Leu Ala Pro Ser Gly Gly Gly Ser
1               5                   10                  15

<210> SEQ ID NO 4
<211> LENGTH: 16
```

```
<212> TYPE: PRT
<213> ORGANISM: Homo sapiens

<400> SEQUENCE: 4

Asn Asn Val Ser Gln Lys Trp Gln Gln Arg Leu Ile Gly Gly Gly Ser
1               5                   10                  15

<210> SEQ ID NO 5
<211> LENGTH: 16
<212> TYPE: PRT
<213> ORGANISM: Homo sapiens

<400> SEQUENCE: 5

Asn Ser Met Ile Ala His Asn Lys Thr Arg Met His Gly Gly Gly Ser
1               5                   10                  15

<210> SEQ ID NO 6
<211> LENGTH: 16
<212> TYPE: PRT
<213> ORGANISM: Homo sapiens

<400> SEQUENCE: 6

Gly Ile His Val Pro Trp Met Pro Pro Val Ala Phe Gly Gly Gly Ser
1               5                   10                  15

<210> SEQ ID NO 7
<211> LENGTH: 16
<212> TYPE: PRT
<213> ORGANISM: Homo sapiens

<400> SEQUENCE: 7

Gln Arg Ser Trp Thr Leu Asp Ser Ala Leu Ser Met Gly Gly Gly Ser
1               5                   10                  15

<210> SEQ ID NO 8
<211> LENGTH: 16
<212> TYPE: PRT
<213> ORGANISM: Homo sapiens

<400> SEQUENCE: 8

Ser Gly His Gln Leu Leu Leu Asn Lys Met Pro Asn Gly Gly Gly Ser
1               5                   10                  15

<210> SEQ ID NO 9
<211> LENGTH: 16
<212> TYPE: PRT
<213> ORGANISM: Homo sapiens

<400> SEQUENCE: 9

Ser Ser Thr Leu Lys Thr Phe Phe Gly Phe Pro Asp Gly Gly Gly Ser
1               5                   10                  15

<210> SEQ ID NO 10
<211> LENGTH: 16
<212> TYPE: PRT
<213> ORGANISM: Homo sapiens

<400> SEQUENCE: 10

Asp Ser Ser Asn Pro Ile Phe Trp Arg Pro Ser Ser Gly Gly Gly Ser
1               5                   10                  15

<210> SEQ ID NO 11
<211> LENGTH: 16
<212> TYPE: PRT
<213> ORGANISM: Homo sapiens
```

-continued

<400> SEQUENCE: 11

Asn Tyr Ser His Leu Arg Val Lys Leu Pro Thr Pro Gly Gly Gly Ser
1               5                   10                  15

<210> SEQ ID NO 12
<211> LENGTH: 16
<212> TYPE: PRT
<213> ORGANISM: Homo sapiens

<400> SEQUENCE: 12

Ser Gly His Gln Leu Leu Leu Asn Lys Met Pro Asn Gly Gly Gly Ser
1               5                   10                  15

<210> SEQ ID NO 13
<211> LENGTH: 16
<212> TYPE: PRT
<213> ORGANISM: Homo sapiens

<400> SEQUENCE: 13

Ala Thr Trp Ser His His Leu Ser Ser Ala Gly Leu Gly Gly Gly Ser
1               5                   10                  15

<210> SEQ ID NO 14
<211> LENGTH: 16
<212> TYPE: PRT
<213> ORGANISM: Homo sapiens

<400> SEQUENCE: 14

Ser Tyr Ser Gln Met Asp Pro Pro Arg Ser Leu Pro Gly Gly Gly Ser
1               5                   10                  15

<210> SEQ ID NO 15
<211> LENGTH: 12
<212> TYPE: PRT
<213> ORGANISM: Homo sapiens

<400> SEQUENCE: 15

Thr Met Arg Asn Pro Ile Thr Ser Leu Ile Ser Val
1               5                   10

<210> SEQ ID NO 16
<211> LENGTH: 12
<212> TYPE: PRT
<213> ORGANISM: Homo sapiens

<400> SEQUENCE: 16

Leu Leu Ala Asp Thr Thr His His Arg Pro Trp Thr
1               5                   10

<210> SEQ ID NO 17
<211> LENGTH: 12
<212> TYPE: PRT
<213> ORGANISM: Homo sapiens

<400> SEQUENCE: 17

Lys Glu Ile Pro Pro Ile Pro Leu Leu Ala Pro Ser
1               5                   10

<210> SEQ ID NO 18
<211> LENGTH: 12
<212> TYPE: PRT
<213> ORGANISM: Homo sapiens

<400> SEQUENCE: 18

Asn Asn Val Ser Gln Lys Trp Gln Gln Arg Leu Ile
1               5                   10

<210> SEQ ID NO 19
<211> LENGTH: 12
<212> TYPE: PRT
<213> ORGANISM: Homo sapiens

<400> SEQUENCE: 19

Asn Ser Met Ile Ala His Asn Lys Thr Arg Met His
1               5                   10

<210> SEQ ID NO 20
<211> LENGTH: 12
<212> TYPE: PRT
<213> ORGANISM: Homo sapiens

<400> SEQUENCE: 20

Gly Ile His Val Pro Trp Met Pro Pro Val Ala Phe
1               5                   10

<210> SEQ ID NO 21
<211> LENGTH: 12
<212> TYPE: PRT
<213> ORGANISM: Homo sapiens

<400> SEQUENCE: 21

Gln Arg Ser Trp Thr Leu Asp Ser Ala Leu Ser Met
1               5                   10

<210> SEQ ID NO 22
<211> LENGTH: 12
<212> TYPE: PRT
<213> ORGANISM: Homo sapiens

<400> SEQUENCE: 22

Ser Gly His Gln Leu Leu Asn Lys Met Pro Asn
1               5                   10

<210> SEQ ID NO 23
<211> LENGTH: 12
<212> TYPE: PRT
<213> ORGANISM: Homo sapiens

<400> SEQUENCE: 23

Ser Ser Thr Leu Lys Thr Phe Phe Gly Phe Pro Asp
1               5                   10

<210> SEQ ID NO 24
<211> LENGTH: 12
<212> TYPE: PRT
<213> ORGANISM: Homo sapiens

<400> SEQUENCE: 24

Asp Ser Ser Asn Pro Ile Phe Trp Arg Pro Ser Ser
1               5                   10

<210> SEQ ID NO 25
<211> LENGTH: 12
<212> TYPE: PRT
<213> ORGANISM: Homo sapiens

<400> SEQUENCE: 25

Asn Tyr Ser His Leu Arg Val Lys Leu Pro Thr Pro

-continued

```
<210> SEQ ID NO 26
<211> LENGTH: 12
<212> TYPE: PRT
<213> ORGANISM: Homo sapiens

<400> SEQUENCE: 26

Ser Gly His Gln Leu Leu Leu Asn Lys Met Pro Asn
1               5                   10

<210> SEQ ID NO 27
<211> LENGTH: 12
<212> TYPE: PRT
<213> ORGANISM: Homo sapiens

<400> SEQUENCE: 27

Ala Thr Trp Ser His His Leu Ser Ser Ala Gly Leu
1               5                   10

<210> SEQ ID NO 28
<211> LENGTH: 16
<212> TYPE: PRT
<213> ORGANISM: Homo sapiens

<400> SEQUENCE: 28

Ser Tyr Ser Gln Met Asp Pro Pro Arg Ser Leu Pro Gly Gly Gly Ser
1               5                   10                  15
```